United States Patent
Gertner

(12) 
(10) Patent No.: US 7,544,177 B2
(45) Date of Patent: Jun. 9, 2009

(54) AEROSOL DEVICE TO DELIVER BIOACTIVE AGENT

(75) Inventor: Michael E. Gertner, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 960 days.

(21) Appl. No.: 10/350,809

(22) Filed: Jan. 24, 2003

(65) Prior Publication Data

US 2003/0181917 A1    Sep. 25, 2003

Related U.S. Application Data

(60) Provisional application No. 60/350,464, filed on Jan. 24, 2002.

(51) Int. Cl.
*A61M 37/00* (2006.01)

(52) U.S. Cl. .................................................. 604/24

(58) Field of Classification Search ............. 604/23, 604/24, 26, 27, 82–87, 58
See application file for complete search history.

(56) References Cited

U.S. PATENT DOCUMENTS

| | | | |
|---|---|---|---|
| 3,589,363 A | 6/1971 | Banlo et al. | |
| 4,427,650 A | 1/1984 | Stroetmann | |
| 4,631,055 A | 12/1986 | Redl et al. | |
| 4,752,466 A | 6/1988 | Saferstein et al. | |
| 5,558,646 A | 9/1996 | Roche | |
| 5,582,596 A | 12/1996 | Fukunaga et al. | |
| 5,605,541 A | 2/1997 | Holm | |
| 5,697,947 A * | 12/1997 | Wolf et al. | 606/185 |
| 5,707,402 A * | 1/1998 | Heim | 607/88 |
| 6,117,150 A | 9/2000 | Pingleton et al. | |
| 6,165,201 A * | 12/2000 | Sawhney et al. | 606/214 |
| 6,394,975 B1 | 5/2002 | Epstein | |
| 6,454,786 B1 | 9/2002 | Holm et al. | |
| 6,461,325 B1 * | 10/2002 | Delmotte et al. | 604/82 |
| 6,461,361 B1 | 10/2002 | Epstein | |
| 6,478,754 B1 | 11/2002 | Babeav | |
| 6,641,800 B1 | 11/2003 | Mistry et al. | |
| 6,716,190 B1 * | 4/2004 | Glines et al. | 604/70 |
| 2003/0108511 A1 | 6/2003 | Sawhney | |

FOREIGN PATENT DOCUMENTS

| | | |
|---|---|---|
| EP | 0 738 498 A1 | 4/1996 |
| WO | WO 97/20585 A1 | 6/1997 |
| WO | WO 02/053014 A2 | 7/2002 |

* cited by examiner

*Primary Examiner*—Manuel A Mendez
(74) *Attorney, Agent, or Firm*—Weaver Austin Villeneuve & Sampson LLP; Tom Hunter

(57) ABSTRACT

This invention provides surgical devices and methods to apply bioactive agents to surgical sites. The devices include, e.g., a body for attachment of a pressurized fluid vessel and a reservoir of bioactive agent for controlled spraying of an aerosol of bioactive agent.

25 Claims, 5 Drawing Sheets

AEROSOL DEVICE TO DELIVER BIOACTIVE AGENT

CROSS-REFERENCE TO RELATED APPLICATIONS

This application claims priority to and benefit of, U.S. Ser. No. 60/350,464, filed on Jan. 24, 2002 which is incorporated herein by reference in its entirety for all purposes.

STATEMENT AS TO RIGHTS TO INVENTIONS MADE UNDER FEDERALLY SPONSORED RESEARCH AND DEVELOPMENT

[NOT APPLICABLE]

FIELD OF THE INVENTION

The present invention is in the field of surgical devices to clear the operating field and for application of bioactive agents to a surgical site. The devices of the invention provide a stream of pressurized gas to strip away latent surgical fluids, and expose wounds or tissue surfaces. Bioactive agents can be drawn into the stream of gas and directed to the surgical site, even in the close confines of laparoscopic surgery.

BACKGROUND OF THE INVENTION

A major challenge in surgical operations has been control of blood flow. The presence of pooled blood at the surgical site can obscure a surgeon's view. Significant loss of blood can lead to shock and threaten the life of the patient. Many techniques to stop or reduce blood flow in surgery have been devised, but such techniques are often ineffective in conditions experienced during minimally invasive surgeries.

Among the techniques available to a surgeon for control of bleeding during surgery are suture ligation (stitches), electrocautery, argon bean coagulation, surgical clips, and application of pressure. These methods used alone, or in combination, can successfully control bleeding in many circumstances. However, these methods can be tedious and can distract the surgeon from the primary surgical task. Many of these techniques are ineffective or impractical in the case of laparoscopic surgery.

Recently, the application of coagulation potentiators has been used to help control bleeding during and after surgery. These potentiators can interact with platelets, and/or the coagulation cascade proteins of plasma, to provide blood flow barriers that promote healing and can dissolve during convalescence. Coagulation potentiators include fibrin glues, collagen sponges, artificial sponges, and the like. In many cases, these coagulation potentiators can be applied generally to stop multiple small bleeding sites or to stop bleeding at sites not localized with certainty. These coagulation potentiators commonly require a cleared and dried site for application. Although gross blood can be removed by suction, this practice may not be compatible with laparoscopic surgery. In addition, suction devices work locally on pooled fluids but can clog or seal on tissues, and are poorly suited to clearing and drying many surgically exposed surfaces.

Laparoscopic and robotic surgery have brought unique problems for control of bleeding and adhesions. For example, in laparoscopic surgery, bleeding can not generally be controlled by suctioning or application of pressure. In open incision style surgery, the surgeon could easily manipulate organs to apply coagulation potentiators and antiadhesive films. This is not the case in laparoscopic surgery. It remains difficult to deliver bioactive agents to surgical sites during laparoscopic surgery.

A need remains for methods to clear fluids from tissue surfaces during surgery and for immediate application of bioactive agents, such as hemostatic agents or antiadhesive agents. Portable, sterilizable devices for application of liquid or dry bioactive agents would be beneficial, particularly in the case of laparoscopic surgery. The present invention provides these and other features that will become apparent upon review of the following.

SUMMARY OF THE INVENTION

The present invention provides, e.g., handheld surgical devices, and methods for clearing surgical sites and application of bioactive agents to surgical sites. The device of the invention can include, e.g., a device body for connection of a pressurized fluid source and a reservoir of bioactive agent, which can be controllably released as an aerosol through an outlet port. The methods of the invention include, e.g., coupling a reservoir of bioactive agent to a device of the invention and activating the device to apply a the aerosol of bioactive agent in a stream of the pressurized fluid onto a surgical site. The devices and methods of the invention can be suitable, e.g., for use in minimally invasive surgeries.

A handheld surgical device of the invention can include, e.g., a means for receiving a pressurized fluid vessel, a means for receiving a reservoir, an outlet port, a valve can regulates flow of a pressurized fluid through the means for receiving a pressurized fluid vessel, and a channel. The channel can communicate between the means for receiving a pressurized fluid vessel, the means for receiving a reservoir, and the outlet port. The channel can have a mixing chamber where fluid, passing from the means for receiving a pressurized fluid vessel to the outlet port, mixes with a bioactive agent flowing from the means for receiving a reservoir resulting in the agent and the fluid exiting the device through the outlet port. A pressurized fluid vessel and/or a reservoir of bioactive agent can be affixed to the means for receiving to supply constituents of the aerosol mixture. The handheld surgical device can have a hand grip. In one embodiment, the surgical device is a body with a removably or permanently affixed pressurized fluid chamber; a means for receiving a reservoir; an outlet port; and, a channel that communicates between pressurized fluid chamber, the means for receiving a reservoir, and the outlet port. The channel has a Venturi constriction so that a gas passing from the means for receiving a pressurized fluid vessel to the outlet port aspirates a bioactive agent, resulting in an agent/fluid aerosol exiting the device through the outlet port. In another embodiment, the bioactive agent can be suspended or dissolved in the pressurized fluid (such as carbon dioxide, nitrogen, argon, helium, or compressed air) in the pressurized fluid vessel, a nozzle is in fluid communication with the pressurized fluid vessel, and the flow rate of pressurized fluid from the vessel through the nozzle is regulated with a valve.

The means for receiving vessels and/or reservoirs can be, e.g., standard means of sealably affixing containers and/or conduit, known in the art. For example, the means for receiving can be threaded connections, beveled connections, clipped connections, quick-release connections, resilient connections, welded connections, glued connections, molded connections, and/or the like.

The pressurized fluid vessel can, e.g., retain a pressurized fluid for controllable release of a gas stream into the channel of the device. The vessel can be permanently or removably affixed to the device body at the means for receiving said pressurized fluid vessel. The vessel can optionally be integral to the device body. The pressurized fluid vessel can contain a pressurized fluid, such as, e.g., carbon dioxide, nitrogen, argon, helium, atmospheric air, liquefied gasses, liquid propellants, and/or the like. Release of pressurized fluid to form a stream of flowing gas through the channel can be regulated by a valve functionally mounted at a location between the pressure vessel and exterior of the device. The vessel can include, e.g., a means, such as a spring loaded one-way valve, a ball valve, and the like, for connecting a pressurized gas source to the vessel in order to charge the vessel with pressure.

The reservoir can, e.g., contain a bioactive agent for regulated release into a gas stream to form an aerosol of dry particles and/or liquid droplets. The reservoir can be permanently or removably affixed to the device body at the means for receiving a reservoir. The bioactive agents can include, e.g., hemostatic agent, an adhesion preventing compound, a nucleic acid, a protein, a muscle contraction stimulator, an anti-inflammatory compound, a vaccine, an enzyme, a growth factor, a nanoparticle, and/or the like. Typical hemostatic bioactive agents of the device can include, e.g., collagen, fibrin, thrombin, fibrinogen, tissue factor, a non-organic hemostasis activator, and/or the like. Typical adhesion-preventing agent can include, e.g., polyethylene glycol and derivatives, polylactic acid, polyglycolic acid, hyaluronic acid, paclitaxel and derivatives, sirolimus and derivatives, and/or the like. The bioactive agent can be associated with a carrier macromolecule. The bioactive agent can be pegylated.

The gas stream and bioactive agent can be mixed, e.g., within the channel of the device and/or within the mixing chamber. A means for regulating the mixing proportions between an agent from the reservoir attached to the means for attaching a reservoir and fluid from pressurized fluid vessel can be incorporated into the device. For example, the rate of release of fluid from the pressurized fluid vessel can be regulated to control the rate of gas streaming past the means for receiving a reservoir. The bioactive agent can be aspirated, with or without the aid of a Venturi constriction, into the channel by a relatively low pressure generated by the gas stream flowing past the means for receiving a reservoir. Aspiration can vary with the flow rate of the gas stream. An adjustable aperture, or other means for a for regulating the rate of aspiration of an agent from reservoir can regulate mixing proportions. The aperture can be adjustable, e.g., from substantially non-communicating with the channel to a position of open communication with the channel.

The outlet port can release, e.g., a controlled and directed jet of gas or aerosol onto a surgical site. The outlet port can have, e.g., an adjustable and/or removable nozzle attached. The outlet or nozzle can include, or functionally interact with, a tube adapted to direct outlet gas and/or aerosol into a laparoscopic surgical site through a trocar. The device can have any of a variety of flexible extensions associated with the outlet port and suitable for insertion through an endoscope, bronchoscope, arthroscope, ureteroscope, catheter, or vascular access device.

The device can be fabricated from materials, such as, e.g., metal, polymer, and/or ceramic. The device can be designed to be substantially sterilized. For example, the device can be tolerant of the temperature and moisture in an autoclave. The device can be tolerant of ionizing radiation and/or microwave radiation.

The present invention includes kit, e.g., comprising a device of the invention and facilitating practice of the methods of the invention. The kits of the invention can be a container containing a device of the invention for use in clearing an operative field and/or administering a bioactive agent. The kit can be substantially sterilizable, e.g., made of materials tolerant of the temperature and moisture in an autoclave, tolerant of ionizing radiation, and/or tolerant of radiation produced within a microwave oven. The kits of the invention can include instructional materials teaching the use of devices of the invention to clear an operative field and/or to administer a bioactive agent to a tissue in the operative field.

In another embodiment of the kits for administering a bioactive agent to a tissue, the kit includes a reservoir containing a dry bioactive agent formulated to aerosolize in a fluid stream. The reservoir has a means for removable attachment to a device of the invention. The kit can also contain the device. The reservoir can have, e.g., a means for regulating the rate of aspiration of the bioactive agent from the reservoir, as is typical of the devices of the invention.

The kits can be provided with a liquid of dry bioactive agent. For example, the bioactive agent can be a hemostatic agent, such as collagen, fibrin, thrombin, or fibrinogen. The bioactive agent can be, e.g., an adhesion-preventing agent, such as polyethylene glycol and derivatives, polylactic acid, polyglycolic acid, or hyaluronic acid. The bioactive agent can be associated with a macromolecule.

The present invention includes methods of locally administering a bioactive agent. The methods of the invention can include, e.g., coupling a reservoir containing a bioactive agent to any of the devices described herein, and activating the device to apply the bioactive agent as an aerosol onto a surgical site. For example, a reservoir of bioactive agent can be aspirated within an activated device having a Venturi constriction, and/or a mixing chamber, to be sprayed onto a surgical site as an aerosol. Optionally the bioactive agent can be premixed with a pressurized fluid and sprayed directly onto a surgical site under the control of a valve.

The pressurized fluid can be released through the outlet port providing a stream of flowing gas to clear fluids from the surgical site. The stream of gas can be used to dry the site, e.g., in preparation for application of the bioactive agent.

An aerosol can be released from the outlet port to apply bioactive agent to the surgical site. In the methods, the aerosol can be, e.g., a suspension of bioactive agent in a fluid stream of carbon dioxide gas. The bioactive agent can be a hemostatic agent and directed at a bleeding surface. The hemostatic agent can be, e.g., collagen, fibrin, thrombin, fibrinogen, tissue factor, or a non-organic surface to promote hemostasis indirectly. The fluid stream can be directed to a surface of bowel, peritoneum, heart, lungs, spleen, pancreas, colon, stomach, muscle, thyroid gland, parathyroid gland, brain, adrenal gland, prostate gland, esophagus, ureteral tract, and/or the like. The bioactive agent can be, e.g., an adhesion-preventing agent, such as , e.g., polyethylene glycol and derivatives, polylactic acid, polyglycolic acid, hyaluronic acid, rapamycin (sirolimus), paclitaxel, and cyclosporine. The bioactive agent can be in a liquid form or a substantially dry form while held in the reservoir.

In another embodiment of the method, the reservoir of bioactive agent is coupled to any device of the invention, the device activated, and the combination of pressurized fluid and bioactive agent is applied with sufficient momentum to substantially penetrate the surface of an organ. The organ can be, e.g., liver, kidneys, small bowel, colon, rectum, lungs, heart, brain, spleen, or pancreas. The bioactive agent can be a gene plasmid, a complementary mRNA, or an interfering double stranded RNA.

Definitions

The term "bioactive agent" as used herein refers to one or more agents that, when administered to a cell, tissue, or organism, alter one or more physiological processes in that cell, tissue, or organism. Preferably, the alteration is a medically desirable alteration.

The term "pressurized fluid" refers to a gas, and/or a liquid, and/or a liquid form of a gas (e.g. a supercritical gas).

DETAILED DESCRIPTION

The present invention provides devices and methods, e.g., to clear fluids from a surgical site and/or to apply bioactive agents to the site. In certain embodiments, the devices of the invention include, e.g., handheld surgical devices having a source of pressurized fluid and a source of bioactive agent in fluid communication with an outlet port so that a stream of the fluid and/or an aerosol of the agent can be directed in a spray onto the surface of a surgical site. The devices described herein can be used in a variety of methods, e.g. to clear an operative field and/or to administer a bioactive agent. In one embodiment, for example, this can be accomplished by loading the bioactive agent into a device of the invention, and directing a stream of gas and/or bioactive agent aerosol onto a surgical site.

In certain embodiments, devices according to this invention generally provide, e.g., a body comprising a channel leading to an outlet port (often comprising a spray nozzle), and a means for functionally connecting a pressure source and/or a reservoir of bioactive agent to the channel, so that a pressurized fluid stream (e.g. a gas stream) and/or an aerosol comprising the bioactive agent can be controllably released. The pressure source and/or the bioactive agent reservoir can be removable and/or permanently affixed to the body.

In certain embodiments the device comprises a removable or permanently affixed pressurized fluid vessel and a separate removable or permanently affixed reservoir for a bioactive agent. The device can additionally comprise a mixing chamber where the bioactive agent mixes with the pressurized fluid (e.g. $CO_2$). In certain embodiments, the bioactive agent can be aspirated into a stream of gas by Venturi action. In other embodiments, the bioactive agent can be premixed with pressurized gas in a liquid form for near supercritical spraying. Valves can be incorporated into the device to control flow of the pressurized fluid, control aspiration of the bioactive agent, and/or to control venting of the bioactive agent reservoir.

Figure 1A:
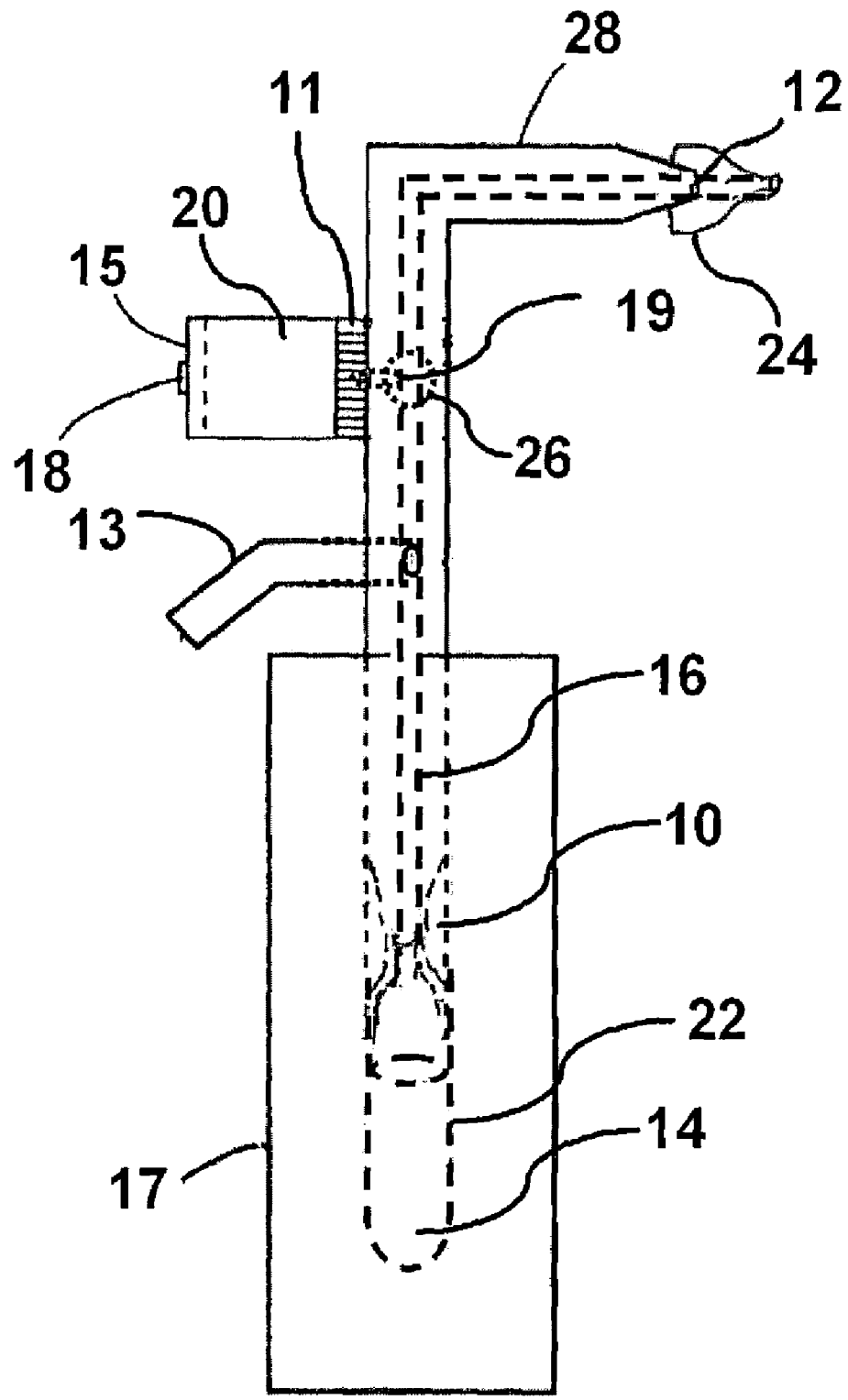
FIG. 1A is a schematic diagram of a hand held surgical device of the invention.

In one embodiment of the invention, as shown in FIG. 1A, the device can comprise a body 17 with means 10 for receiving a pressurized fluid vessel 22, means 11 for receiving a reservoir 15 optionally containing a bioactive agent 20, an outlet port 12 optionally bearing a fixed or adjustable nozzle 24, and a control valve 13 that regulates flow of the pressurized fluid 14 from the pressurized vessel 22 through channel 16 in body 17, and optional tube 28, and out through the outlet port 12. The device can have the pressurized fluid vessel connected to the means for receiving a pressurized vessel. Similarly, the reservoir 15 of bioactive agent, when present, can be connected to the means 11 for receiving a reservoir 15.

Pressurized fluid (typically a compressed, liquid or supercritical gas) from the vessel can mix, in a mixing chamber 26, with a bioactive agent 20 from the reservoir 15 and exit as an aerosol spray from the outlet port. The body can act as a fluid flow control manifold with vessels and/or reservoirs detachable or permanently mounted to their respective receiving means.

The device can optionally include, e.g., valves and/or adjustable ports allowing control of reservoir venting, bioactive agent flow, and/or pressurized gas flow. Flow of bioactive agent into the flow of pressurized fluid in the body channel can be, e.g., by aspiration, e.g., through an aperture at a Venturi constriction 19 that can be functionally associated with the means for receiving a reservoir and/or with the mixing chamber 26 at the channel.

Figure 1B:
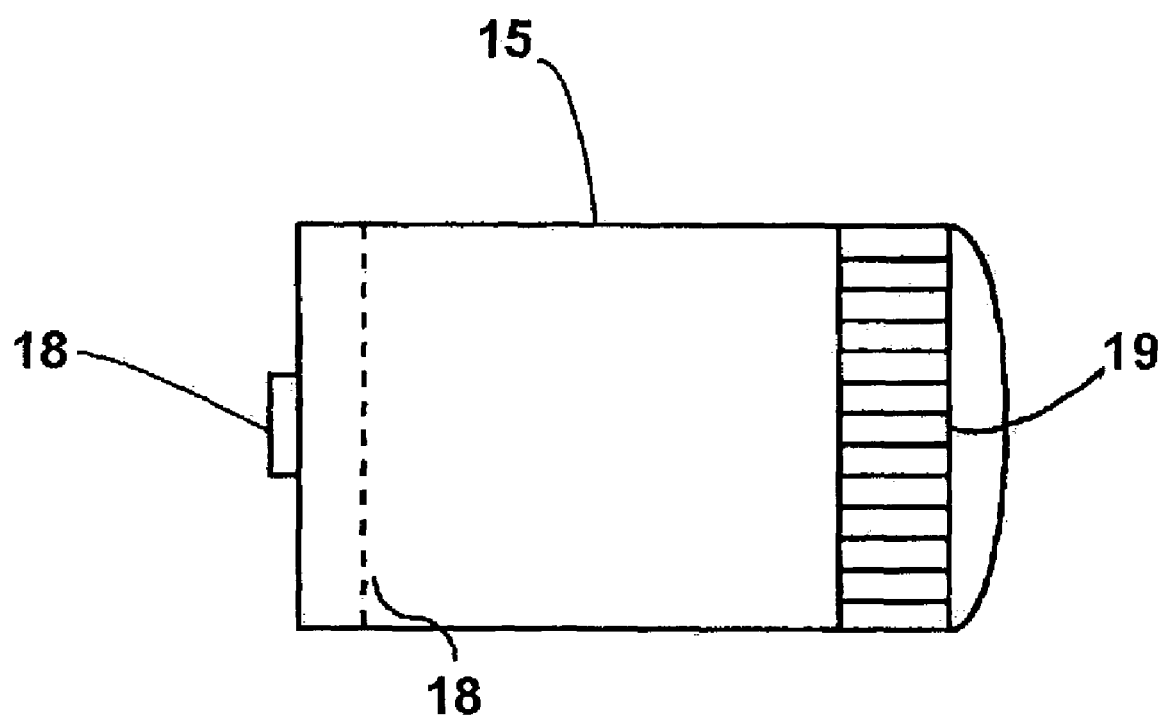
FIG. 1B shows a schematic diagram of a bioactive agent reservoir fixable to the device.

Optionally, the bioactive agent can be suspended or dissolved in a pressurized fluid, such as a near supercritical gas. In certain embodiments, the pressurized fluid comprising the bioactive agent is held in the reservoir 15 as illustrated in FIG 1B. While the pressurized reservoir can be used in conjunction with the pressurized fluid vessel 22, use of a pressurized reservoir combining both the bioactive agent(s) and the pressurized fluid, can obviate the need for a separate pressurized fluid vessel 22. In such "single chamber" embodiments, the suspension or solution of bioactive agent is held in a pressurized reservoir and can be expelled through the channel 16 under control of a valve 13.

The device body, vessel, reservoir, valves, and other components of the devices can be fabricated from materials suitable to the functions and conditions of use for the device. For example, the components can be fabricated from of metals, polymers, composites, ceramics, and/or the like. In certain preferred embodiments, the devices can be fabricated from autoclavable and/or radiotolerant materials capable of being substantially sterilized by methods common in the art.

The body of the handheld surgical devices of the invention can act, e.g., to interconnect other components of the device through valve controlled manifolds. For example, the body can receive the bioactive agent reservoir, the pressurized fluid vessel and/or a spray nozzle. The body can provide valves to control flow from the reservoir and the vessel through a mixing chamber and out a nozzle at the outlet port.

The body can comprise receiving means for vessels and reservoirs, in fluid contact with the channel. The receiving means can receive vessels and/or reservoirs permanently or detachably. Receiving means capable of detachment can include any connection means known in the art, such as, e.g., threaded connections, beveled connections, clipped connections, quick-release connections, resilient connections, and/or the like. Permanent receiving means can include, e.g., fittings suitable for welding, gluing, or molding vessels or reservoirs to the body.

The body can have a channel connecting, e.g., the receiving means to the outlet port through a mixing chamber. The channel can be in fluid contact with a vessel of pressurized fluid through a means for receiving a pressurized fluid vessel so that released fluid flows past a means for receiving a reservoir in such a way as to create a relative low pressure capable of aspirating contents from the reservoir into the fluid (Venturi effect). A Venturi constriction can be located in the channel at the point where the released fluid passes the means for receiving a reservoir, to increase the efficiency of aspiration according to Bernoulli's Principle.

The body channel (e.g., 16 in FIG. 1A) can be configured to provide a mixing chamber to mix bioactive agents into the stream of gas. For example, flow of gas in the channel can be disturbed down stream from the point where bioactive agent is introduced into the gas to further volatilize the bioactive agent(s). The mixing chamber can be, e.g., simply a section of channel between the means of receiving the reservoir and the outlet, without particular modifications to enhance mixing. In one embodiment, the mixing chamber comprises a zone of increased internal diameter along the path of the channel. In another embodiment, the mixing chamber comprises an area within the channel containing baffles, vanes, beads, strakes, fenestrations, and/or the like to generate vortices or chaotic flow in the stream of gas and agent.

The device body 17 can incorporate valves and/or other means to regulate flow rates from vessels and/or reservoirs of the device. Such flow regulating means can, e.g., adjust the absolute quantities and/or mixing proportions of pressurized gas and bioactive agents. For example, the body can have a valve located along the flow channel to control the rate of pressurized gas flow. In certain embodiments, the rate of bioactive agent incorporation into the pressurized fluid stream can be regulated, e.g., by providing an adjustable outlet aperture and/or vent in the reservoir. For example, the reservoir can comprise a means for regulating the rate of aspiration of an agent in which an aperture, adjustable from substantially non-communicating to a position of open communication with the channel, is located between the channel of flowing gas and the reservoir internal space. With the aperture closed (substantially non-communicating) pressurized gas can be sprayed onto a surgical site to clear fluids without application of bioactive agents. The proportion of bioactive agent aspirated into the stream of gas can be adjusted by varying how far the aperture is opened. Vent valve 18, as shown in FIG. 1A, can have a controlling effect on flow of liquid or powder bioactive agent into the channel by regulating the venting of air replacing agents aspirated from the reservoir. In one embodiment, a two-stage trigger can be incorporated into the device whereby, e.g., as the trigger is pulled, increasing amounts of gas are released; when the trigger reaches a certain point, increasing amounts of bioactive agent are released into the gas stream.

A handgrip can be provided in the device of the invention to provide comfortable and functional control to the surgeon or other operator. The body of the device can be in the form of a handgrip, such as is commonly appreciated by those skilled in the art. For example, the body can have, e.g., a cylindrical shape about the length of a palm width and/or a knurled texture for a friction grip. Optionally, a handgrip can be formed into the pressurized fluid vessel or provided as an independent grip affixed to the device.

The pressurized fluid vessel (e.g. 22 in FIG. 1A) can provide, e.g., a portable source of pressurized fluid for release as a stream of gas in the devices of the invention. The vessel can be fabricated from materials suitable for containment of pressurized fluids. Such materials include, but are not limited to such as stainless steel or other metals, or fiber composites, to contain high pressures, e.g., ranging from about 1000 psi to about 3000 psi, to hold, e.g., compressed carbon dioxide, nitrogen, argon, helium, atmospheric air, near supercritical gasses, and/or the like. The vessel can be fabricated from less strong materials where the pressurized fluid originates from common liquid propellants, such as chlorocarbons, fluorocarbons, hydrocarbons, and/or the like. The vessel can be integral to the body or detachable by conventional means.

Where the vessel is detachable, in certain preferred embodiments, the device is removably affixed by a sealable means capable of withstanding the pressure of the fluid within the vessel. Such means are well known to those of skill and include, but are not limited to luer lock fittings, threaded fittings, clipped connections, and the like. It is noted that relatively small (e.g. hand held) pressurized vessels and associated means for sealably affixing such vessels are commercially available.

Figure 1C:
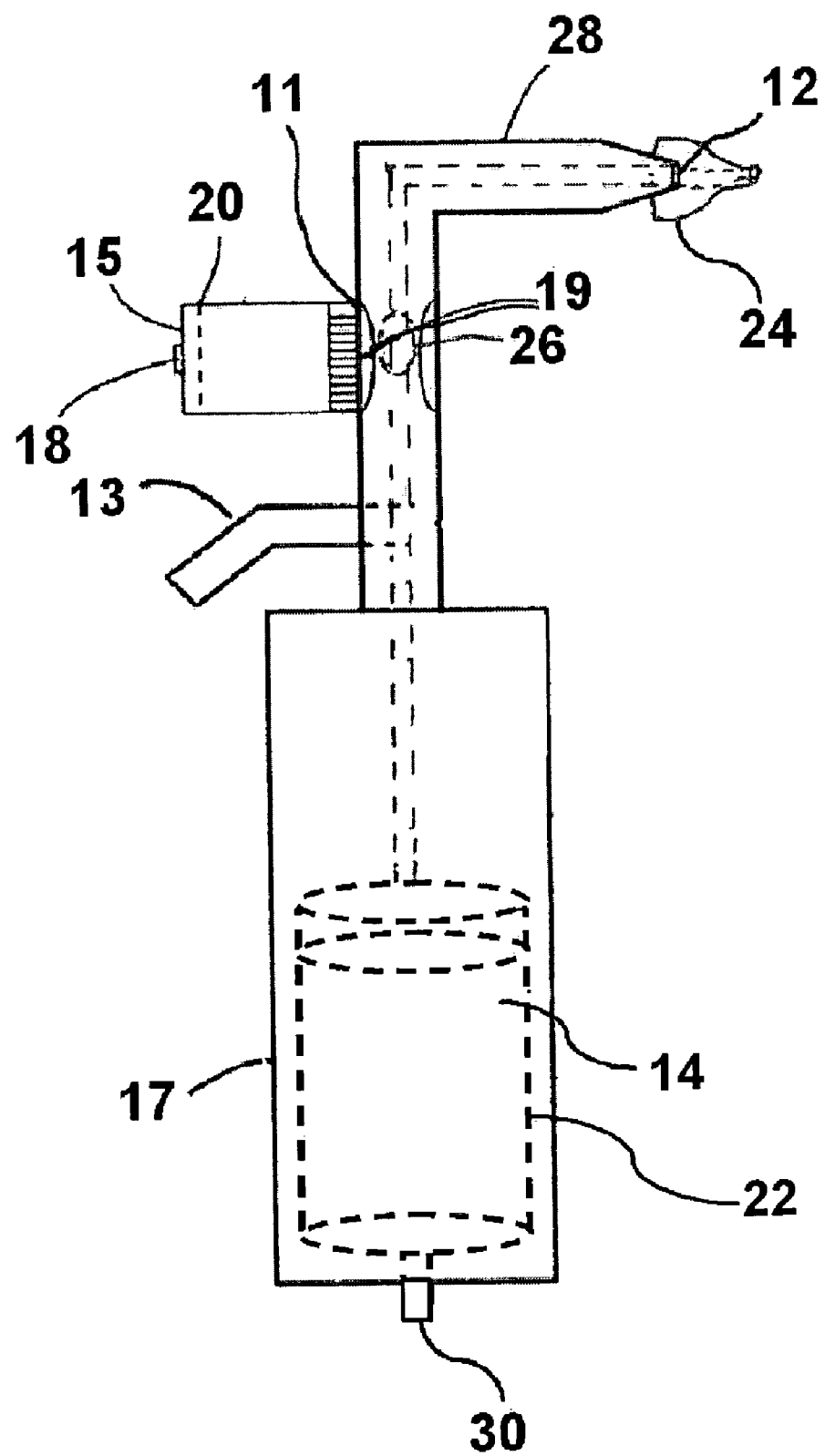
FIG. 1C shows an embodiment where the fluid vessel is integral to the body of the device.

Particularly where the vessel is permanently affixed to the device body 17, and/or is an integral chamber in such a body (e.g. as illustrated in FIG. 1C) the vessel preferably includes a charging port 30, such as a valve stem, through which additional pressurized fluid can be introduced without removal of the vessel from the body. In one embodiment, the "pressurized fluid vessel" can be tubing running to a pressurized gas source external to the hand held device. A control valve can be incorporated into the device to regulate the flow of pressurized fluid from the pressurized fluid vessel. The valve can be of any type known by those skilled in the art, such as needle valves, ball valves, diaphragm valves, seated washer type valves, sluice valves, and the like.

The bioactive agent reservoir typically comprises a container that is sealably received onto or into the body of the handheld surgical device of the invention. The reservoir can, e.g., hold a bioactive agent for regulated introduction into a stream of pressurized fluid (e.g. gas) flowing through a channel in the body channel.

The reservoir (e.g. 15 in FIG. 1A) typically comprises a container affixed permanently or removably to the body at the means for receiving a reservoir. Where the reservoir is removable, means for receiving the reservoir include any separable, sealable connection means known in the art. Such connection means include, but are not limited to threaded connections, beveled connections, clipped connections, quick-release connections, luer lock connections, resilient connections, and the like. Where the reservoir is permanently affixed to the body the reservoir can be an integral chamber of the body (produced e.g. during injection molding of the body), or attached to the body e.g. using welded fittings, glued fittings, and the like. The reservoir can be fabricated from suitable materials known in the art, such as metal, plastic, glass, and/or the like.

Flow of bioactive agents from the reservoir can be regulated as described above. In one embodiment, an aperture is incorporated into the reservoir, channel wall, or Venturi constriction to regulate release of bioactive agent from the reservoir into the flowing stream of gas in the channel and out through the outlet port. The aperture can be adjusted, e.g., from a closed (substantially non-communicating) to a range of open communication settings with the channel. The aperture can be, e.g., an iris type opening, or a valve of any suitable type, such as such as needle valves, ball valves, diaphragm valves, seated washer type valves, sluice valves, and the like. The flow of bioactive agent can be affected by the setting of a vent valve configured to regulate the venting of air to replace agents aspirated from the reservoir. The adjustment of the reservoir aperture and/or vent valve, in combination with the rate of gas flows, can regulate the volume and mixing proportions of gas and agents.

Bioactive agents of the device can include any agent that provides a beneficial prophylactic, therapeutic, and/or hemostatic effect. The bioactive agents can include be, e.g., a hemostatic agent, an adhesion preventing compound, a nucleic acid, a protein, a muscle contraction stimulator, an anti-inflammatory compound, a vaccine, an enzyme, a growth factor, a nanoparticle, a pharmaceutical, and/or the like.

In certain embodiments, the hemostatic agent includes, but is not limited to, e.g., collagen, fibrin, thrombin, fibrinogen, tissue factor, a non-organic hemostasis activator, and/or the like. In certain embodiments, the adhesion-preventing agents include, but are not limited to, e.g., polyethylene glycol and derivatives, polylactic acid, polyglycolic acid, hyaluronic acid, paclitaxel and derivatives, sirolimus and derivatives, and/or the like. The bioactive agents can be formulated in a variety of convenient modalities, e.g., dry powder particles, nanoparticles, in a liquid formulation, etc. In certain embodiments, the bioactive agents can be, e.g., pegylated to increase stability, increase solubility, and/or reduce immunogenicity. The bioactive agents can include, e.g., one or more carriers to increase dispersibility, adjust absorption, pH, viscosity, shelf-life, increase bulk, and/or increase dissolution rates, and the like.

Certain embodiments contemplate the use of multiple bioactive agents in a single reservoir (e.g. a hemostatic agent, and/or an adhesion preventing agent, and/or an antibiotic, etc.). Certain embodiments, contemplate multiple reservoirs each containing a different bioactive agent or agents. Where multiple reservoirs are utilized, they can be utilized on the device sequentially. Alternatively, devices can be provided that accommodate a plurality of reservoirs at the same time.

Gasses and/or aerosols of bioactive agents can exit the handheld surgical device through an outlet port. The outlet port can be configured to eject the gasses or aerosols in a jet directable to target surfaces. The outlet port can be, e.g., fitted with a nozzle that is fixed and/or adjustable to regulate the shape/dispersion of the aerosol spray. The outlet port can be fitted with a tube for insertion through an incision and/or for insertion through a trocar (e.g. during laparoscopic surgery).

In certain embodiments, the nozzle can be removable from the outlet port. The nozzle can be adjustable, e.g., to control the flow rate and/or spray geometry of a gas or aerosol stream.

Figure 2A:
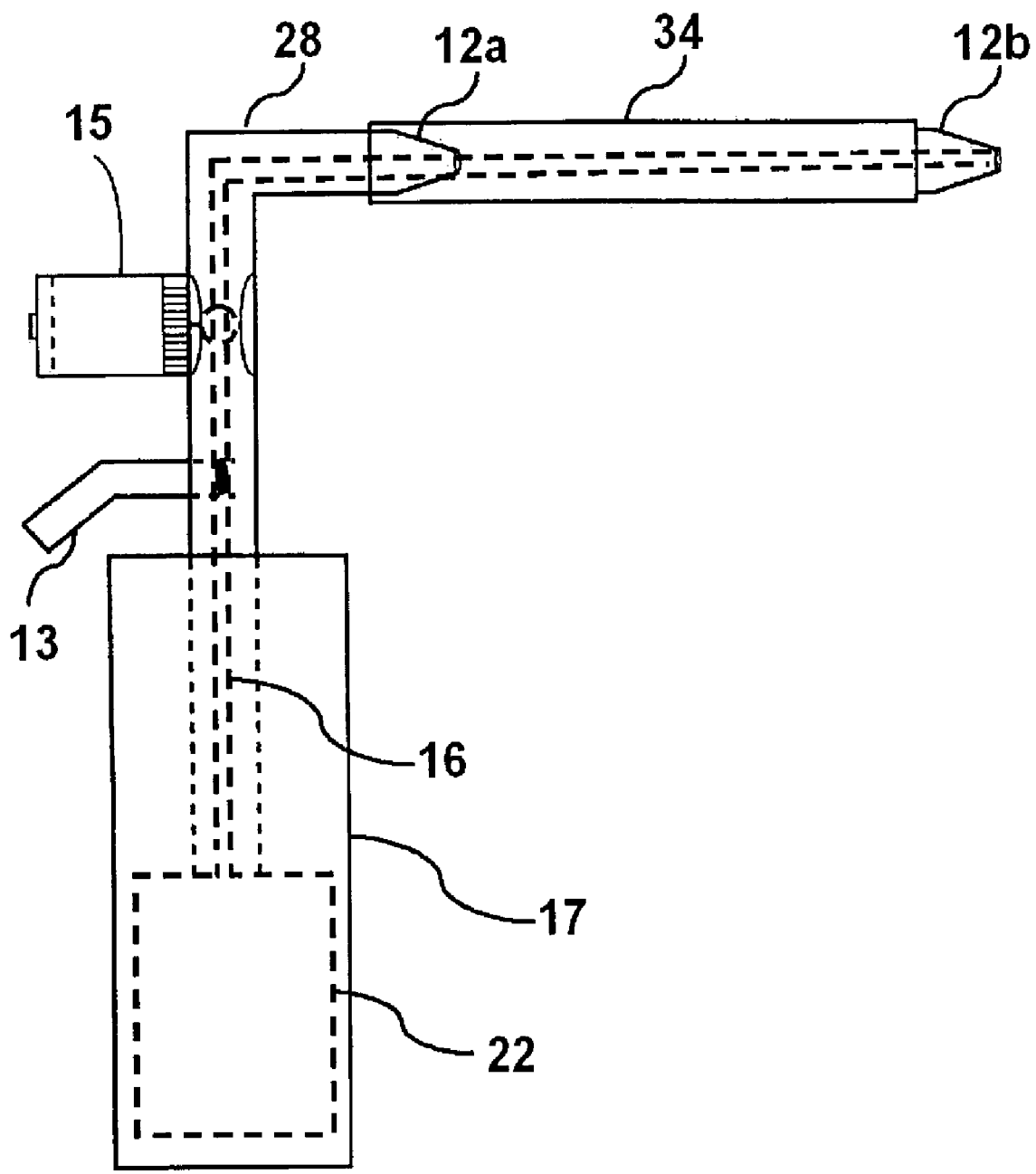
FIGS. 2A and 2B show an embodiment of the device for use in laparoscopic surgery.
Figure 2B:
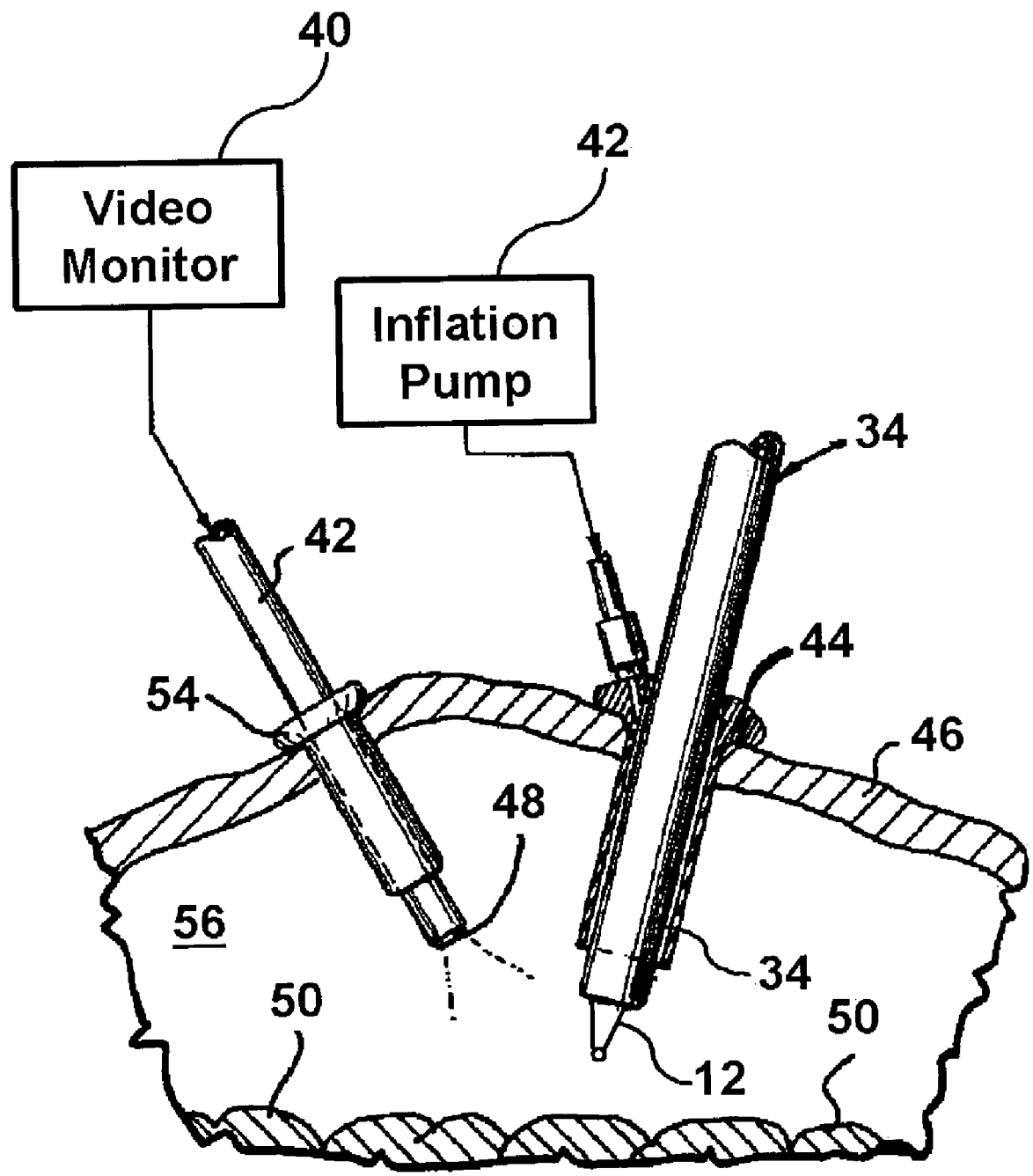

As shown in FIGS. 2A and 2B, a permanently affixed, or removable tube 34 can be fitted around outlet port 12 for insertion through trocar 21 inserted, e.g. into a body surface, during minimally invasive surgery (e.g., laparoscopy). The tube can allow gas and/or aerosol to be directed to surgical surfaces during e.g., a laparoscopic procedure to clear the site or provide homeostasis. The tube can fit closely within the trocar to prevent escape of inflation gases from the surgical cavity, or fit loosely to allow escape of gasses during gas jet clearing or bioactive agent application procedures. The device can have any of a variety of flexible extensions associated with the outlet port and suitable for insertion through an endoscope, bronchoscope, arthroscope, ureteroscope, catheter, or vascular access device.

The devices of this invention can be used to clear/clean, and/or dry a surgical site or portion thereof, and/or to deliver one or more bioactive agents to that site or into a tissue comprising that site.

In FIG. 2B, the device is shown as it would typically be used in a minimally invasive surgical procedure in an abdominal or body cavity 56 in certain embodiments. The device comprising a tube 34 is inserted into the abdominal cavity through a cannula 44 which has previously been passed through the abdominal body or wall 46. An inflation pump 42 forces pressurized and sterile gas, such as carbon dioxide, through the cannula 44 into the abdominal cavity 56. As a result, the abdominal wall 46 expands away from the interior tissues and abdominal organs 50. A pressure sensor of the inflation pump 42 controls the operation of the pump 42 to limit the amount of pressure within the abdominal cavity 56 and thereby limits the amount of expansion of the abdominal wall 46. A second cannula 54, and possibly others as determined by the surgeon, can also be positioned in the abdominal wall 46, but the additional cannulas are not necessarily attached to the inflation pump 42.

A video camera and light source device 48 can be connected to a wand-like device 42. The wand-like device 42 can be inserted into the abdominal cavity 56 through the cannula 54. The light source of the device 48 illuminates the interior tissues and organs 50, and the video camera of the device 48 transmits video images to a video monitor 40. By viewing the interior organs 50, the surgeon is able to manipulate the de device 20 to achieve clear a surface of the site and/or to deliver a bioactive agent.

As indicated above, the device comprises a tube probe 34, optionally terminating in a nozzle 12, as illustrated in FIG. 2C. The device comprises a channel 16 through which gas flow is regulated. Gas flow is regulated by a gas flow control. Gas emerging from the conduit port blows fluid and particulate matter off of one or more surfaces of the surgical site and, optionally dries such surfaces. As desired, the device can also be operated so as to deliver one or more bioactive agents to the surgical site.

As a result of the images on the video monitor 40 obtained from the video camera of the device 48, the surgeon can manipulate the device to position the distal end nozzle 12 at the desired location to achieve the desired surgical effect on the tissue or organs 50.

Bioactive agents can be administered, e.g., locally to a surgical site by coupling a reservoir to a device of the invention, and activating the device to apply a fluid stream of aerosolized bioactive agent to the surgical site. The method can include, e.g., coupling a reservoir of bioactive agent to a device of the invention, and activating the device to apply sufficient momentum to a combination of pressurized fluid and bioactive agent to substantially penetrate the surface of an organ. Bioactive agents can be suspended or dissolved in a pressurized fluid (such as a near supercritical gas) and sprayed through a nozzle under regulation of a control valve.

The devices of the invention can be used to clear fluids from a site for application of bioactive agents. Clearing the site can provide a view of the tissues to be treated and allow direct application or penetration of the agent.

Devices of the invention generally allow, e.g., spraying of a pressurized fluid stream without the presence of a bioactive agent aerosol. This can reduce the consumption of agent and avoid negative effects of general distribution of the agent about the site and surgical suite. The devices optionally provide control of pressure, flow rate and/or spray jet geometry of the pressurized fluid. Such parameters can be adjusted, e.g., to provide stripping or scouring of the surface without undue trauma to the underlying tissues. The flow of gas can dry the site by physical removal of fluids and/or by evaporation of water from the fluids. Drying can be accentuated by provision of gasses with low relative humidity.

In the case of laparoscopic surgery, venting can be provided to allow escape of the clearing and drying gasses. The gasses can escape, e.g., from a space around the device where in enters a patient's body cavity through a trocar, or from a dedicated vent trocar. As body cavities are commonly inflated for easier viewing and manipulations during laparoscopic surgeries, a pressure regulator, such as a spring-loaded poppet valve, can be used to retain a substantially constant pressure in the cavity independent of gas flows during clearing, drying and/or application procedures.

Methods of the invention can be practiced by applying bioactive agents to surgical sites using any of the devices of the invention. Bioactive agents can be loaded into reservoirs, and the reservoirs can be coupled to the body of the device to spray agent onto a surgical site on activation of the device. Agents can be applied to a surface of bowel, peritoneum, heart, lungs, spleen, pancreas, colon, stomach, muscle, thyroid gland, parathyroid gland, brain, adrenal gland, prostate gland, esophagus, ureteral tract, and/or the like. Surfaces beneficially treated can be, e.g., tissues that are inflamed, wounded, infected, abraded, abrided, resected, untraumatized, and/or the like.

The bioactive agents applied in the methods can be, e.g., agents beneficial to the surgical site, such as hemostatic agents, analgesics, antibiotics, antiadhesion agents, and the like. Hemostatic agents for application can include, e.g., activators of the coagulation cascade or platelet aggregation, such as collagen, fibrin, thrombin, and fibrinogen, tissue factor, or a non-organic surface to promote hemostasis indirectly. Such agents can be applied to a bleeding surface or to prevent initiation of bleeding from the a surface. Antiadhesion agents for application include, e.g., polyethylene glycol and derivatives, polylactic acid, polyglycolic acid, hyaluronic acid, rapamycin (sirolimus), paclitaxel, and cyclosporine. Such antiadhesion agents can be beneficially applied, e.g., to external organ membranes, the bowels and peritoneal cavity surfaces. Venting practices can be performed to regulate gas pressures in laparoscopic surgeries.

Bioactive agents can be applied with forces adequate to provide substantial penetration into target tissues. Penetration can be enhanced by, e.g., using pressurized gasses of higher pressures, and/or by using bioactive agents with high density, mass, or penetration enhancing shape. These ballistic application methods can be practiced to insert bioactive agents, such as, e.g., gene plasmids, complementary mRNAs, or an interfering double stranded RNA, into tissues or cells of organs, such as the liver, kidney, small bowel, colon, rectum, lungs, heart, brain, spleen, pancreas, and/or the like.

Kits

In certain embodiments, this invention provides kits for practicing the various methods described herein. In certain embodiments, the kit comprises the surgical device alone (e.g. without a reservoir for a bioactive agent, and/or without a pressurized fluid vessel). In other embodiments, the kits include the surgical device and/or the reservoir for holding a bioactive agent and/or the pressurized fluid vessel. Certain kits will contain only the pressurized fluid vessel and/or the reservoir for holding the bioactive agent. In certain embodiments, the kits comprise a pressurized fluid vessel provided as a cartridge containing a compressed gas (e.g. $CO_2$).

Where the reservoirs are included in the kits, the reservoirs can contain one or more bioactive agents as described herein. In certain embodiments, each reservoir will be loaded so as to contain a single unit dosage of the bioactive agent(s) thereby facilitating easy monitoring of agent dosage. In certain embodiments the bioactive agent is provided in a dry rather than a fluid form so as to increase shelf life.

The kits can be provided with a dry or liquid bioactive agent. The bioactive agent can be substantially sterile, or where the agent is tolerant, packaged for sterilization. The bioactive agent can be provided is a package separate from the device body to allow separate processing, or the bioactive agent can be preloaded to a reservoir received and affixed to the body. The bioactive agent can be, e.g., a macromolecule, such as a polymer or biological molecule. The bioactive agent can be, e.g., a hemostatic agent, such as collagen, fibrin, thrombin, and fibrinogen. The bioactive agent of the kit can be, e.g., an adhesion-preventing agent, such as polyethylene glycol and derivatives, polylactic acid, polyglycolic acid, and/or hyaluronic acid.

The components comprising the kits are typically provided in one or more containers. In certain preferred embodiments, the containers are sterile, or capable of being sterilized (e.g. tolerant of on site sterilization protocols).

The kits can be provided with a dry or liquid bioactive agent. The bioactive agent can be substantially sterile, or where the agent is tolerant, packaged for sterilization. The bioactive agent can be provided is a package separate from the device body to allow separate processing, or the bioactive agent can be preloaded to a reservoir received and affixed to the body. The bioactive agent can be, e.g., a macromolecule, such as a polymer or biological molecule. The bioactive agent can be, e.g., a hemostatic agent, such as collagen, fibrin, thrombin, and fibrinogen. The bioactive agent of the kit can be, e.g., an adhesion-preventing agent, such as polyethylene glycol and derivatives, polylactic acid, polyglycolic acid, and/or hyaluronic acid.

The kits can be provided with instructional materials teaching users how to use the device of the kit. For example, the instructional materials can provide directions on clearing an operative field, drying an operative field, and/or instructions on use of the device to apply bioactive agents to target site, e.g., during laparoscopic surgery.

The instructional materials can also, optionally, teach preferred dosages/therapeutic regiment, counter indication, provide expiration dates, and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A device comprising:
   a body with means for receiving a pressurized fluid vessel;
   a pressurized fluid vessel in communication with said means for receiving a pressurized fluid vessel;
   a means for receiving a reservoir containing a bioactive agent;
   a reservoir containing a bioactive agent in communication with said means for receiving a reservoir containing a bioactive agent;
   a mixing chamber;
   a nozzle in communication with said mixing chamber;
   a valve for regulating the flow of pressurized fluid into said mixing chamber and out said nozzle; and
   a valve for regulating the flow of bioactive agent into said mixing chamber; whereby said device can deliver a pressurized gas stream for cleaning a surgical site and/or a pressurized gas stream containing said bioactive agent, wherein said bioactive agent is selected from the group consisting of a hemostatic agent, an adhesion preventing compound, a nucleic acid, a protein, a muscle contraction stimulator, an anti-inflammatory compound, a vaccine, an enzyme, a growth factor, a nanoparticle, and a pharmaceutical.

2. The device of claim 1, wherein said pressurized fluid is selected from the group consisting of carbon dioxide, nitrogen, argon, helium, and compressed air.

3. The device of claim 1, wherein said one or more bioactive agents comprise a hemostatic agent selected from the group consisting of collagen, fibrin, thrombin, and fibrinogen.

4. The device of claim 1, wherein said one or more bioactive agents comprise an adhesion-preventing agent selected from the group consisting of polyethylene glycol and derivatives, polylactic acid, polyglycolic acid, hyaluronic acid paclitaxel and derivatives, and sirolimus and derivatives.

5. The device of claim 1, wherein said one or more bioactive agents is associated with a macromolecule.

6. The device of claim 1, wherein said nozzle is an adjustable nozzle.

7. The device of claim 1, wherein said nozzle is a removable nozzle.

8. The device of claim 1, wherein said device further comprises a handgrip.

9. The device of claim 1, wherein said device is fabricated from one or more materials selected from the group consisting of metal, polymer, ceramic, and composite.

10. The device of claim 1, wherein said device comprises a nozzle or a nozzle affixed to a tube that can be inserted through a port in a laparoscopic procedure.

11. The device of claim 1, wherein said device comprises a flexible extension suitable for insertion through an endoscope, bronchoscope, arthroscope, ureteroscope, catheter, or vascular access device.

12. The device of claim 1, wherein said device is tolerant of the temperature and moisture in an autoclave.

13. The device of claim 1, wherein said device is tolerant of the radiation in a microwave oven.

14. The device of claim 1, wherein said device is substantially sterile.

15. A method of locally administering a bioactive agent, said method comprising:

coupling a reservoir comprising a bioactive agent to the device of claim 1; and activating said device to apply the bioactive agent as an aerosol onto a surgical site.

16. The method of claim 15, wherein said aerosol is a suspension of bioactive agent in a fluid stream of carbon dioxide gas.

17. The method of claim 15, wherein said activating further comprises operating said device to aspirate said bioactive agent from said reservoir and aerosolize said agent in a fluid stream of gas.

18. The method of claim 17, wherein said fluid stream of gas is directed to a bleeding surface.

19. The method of claim 18, wherein said bioactive agent is a hemostatic agent.

20. The method of claim 19, wherein said bioactive agent is a hemostatic agent selected from the group consisting of collagen, fibrin, thrombin, fibrinogen, tissue factor, and a non-organic surface to promote hemostasis indirectly.

21. The method of claim 15, further comprising clearing or drying the surgical site with a stream of gas from the device.

22. The method of claim 17, wherein said fluid stream is directed to a surface of bowel, peritoneum, heart, lungs, spleen, pancreas, colon, stomach, muscle, thyroid gland, parathyroid gland, brain, adrenal gland, prostate gland, esophagus, or ureteral tract.

23. The method of claim 22, wherein said bioactive agent is an adhesion-preventing agent.

24. The method of claim 23, wherein said bioactive agent is an adhesion-preventing agent selected from the group consisting of polyethylene glycol and derivatives, polylactic acid, polyglycolic acid, hyaluronic acid, rapamycin (sirolimus), paclitaxel, and cyclosporine.

25. The method of claim 15, wherein said bioactive agent is contained within said reservoir in a substantially dry form.

* * * * *